(12) United States Patent
Vogt

(10) Patent No.: US 6,443,938 B1
(45) Date of Patent: Sep. 3, 2002

(54) METHOD OF MAKING A PREFOLDED PREFASTENED DIAPER WITH LATENT ELASTICS

(75) Inventor: Robert Eugene Vogt, Neenah, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 51 days.

(21) Appl. No.: 09/603,714

(22) Filed: Jun. 27, 2000

(51) Int. Cl.[7] ............................................... A61F 13/15
(52) U.S. Cl. .................. 604/391; 604/396; 604/355.27; 604/355.201; 156/164; 156/244.18; 156/522; 156/204
(58) Field of Search ...................... 604/385.201, 385.24, 604/385.25, 385.27, 385.26, 385.02, 391; 156/244.11, 85, 164, 244.18, 244.21, 256, 265, 160, 522, 519

(56) References Cited

U.S. PATENT DOCUMENTS

| | | | |
|---|---|---|---|
| 4,598,528 A | | 7/1986 | McFarland et al. ........... 53/430 |
| 4,650,530 A | * | 3/1987 | Mahoney et al. |
| 4,665,306 A | | 5/1987 | Roland et al. ............... 219/388 |
| 5,080,741 A | * | 1/1992 | Nomura et al. ............. 156/201 |
| 5,330,598 A | * | 7/1994 | Erdman et al. ............. 156/164 |
| 5,536,921 A | * | 7/1996 | Hedrick et al. ............. 219/693 |
| 5,620,780 A | | 4/1997 | Krueger et al. ............. 428/179 |
| 5,879,500 A | * | 3/1999 | Herrin et al. ................ 156/204 |
| 5,916,203 A | * | 6/1999 | Brandon et al. |
| 6,207,941 B1 | * | 3/2001 | Schmidt et al. ............. 219/690 |

FOREIGN PATENT DOCUMENTS

| | | | |
|---|---|---|---|
| EP | 689 816 A2 | 1/1996 | ........... A61F/13/15 |
| WO | 99/01098 | 1/1999 | ........... A61F/13/15 |
| WO | 99/22686 | 5/1999 | ........... A61F/13/15 |

\* cited by examiner

Primary Examiner—John G. Weiss
Assistant Examiner—Jacqueline F Stephens
(74) Attorney, Agent, or Firm—Pauley Petersen Kinne & Erickson

(57) ABSTRACT

A method of making a prefolded diaper or other undergarment includes the steps of forming a web of diaper material, placing a fastening system divided between front and back waist sections onto each diaper section of the web and cutting the web to define individual diapers. The diapers are then folded in half at the crotch section and are then microwaved in a high power resonant cavity microwave device to activate the latent elastic portions which are buried within the folded diaper. Where desired, the refastenable fastening system of the diaper, or the front and back waist sections or the diaper, may be registered in a fastening alignment and fastened together when the diaper is folded to create diapers which are useful upon removal from the point of sale container as pull on training pants.

23 Claims, 3 Drawing Sheets

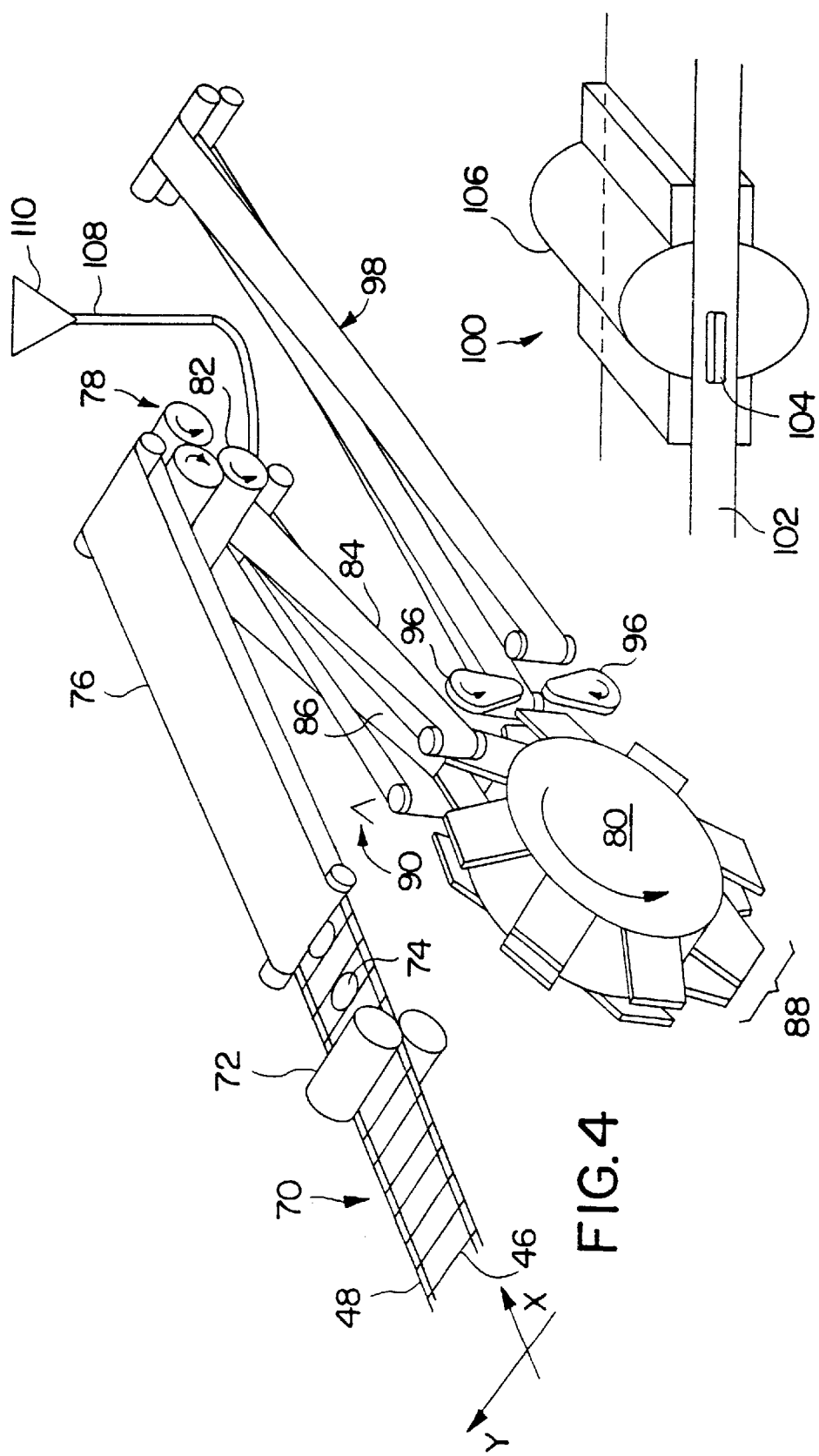

METHOD OF MAKING A PREFOLDED PREFASTENED DIAPER WITH LATENT ELASTICS

BACKGROUND OF THE INVENTION

1. Field of the Invention

The present invention relates to materials having elasticized portions and methods of making the same. More particularly, the present invention relates to absorbent garments, such as disposable diapers and adult incontinence garments, which include such materials and which are configured to absorb and contain body exudates and prevent leakage.

2. Discussion of the Related Art

Elastic shirring of garments in selected regions is desirable or essential to conform the garment to the wearer's body such as at the waist or leg. For example, conventional absorbent articles, such as disposable diapers, employ elasticized waistbands and leg cuffs to help conform the article to the wearer and reduce the leakage of body exudates. Some conventional absorbent articles have also included elasticized containment or barrier flaps at the leg or waist sections of the article to further reduce leaks.

It is know to activate the latent elastic portion of a diaper with microwave energy. Such activation is taught in U.S. Pat. No. 5,916,203, to Brandon et al., for flat web applications involving preconstructed, laid-open diapers. The teachings of the Brandon et al. patent, of common ownership herewith, are incorporated by reference to the extent necessary to derive an understanding of the present invention.

It is also known in the art to fold the preconstructed diaper in such a manner as to register its front and rear waist sections, or waist band areas, in order to seam them and provide a pull-on garment. Various applications by the assignee hereof have suggested registration of front and rear diaper sections in order to prefasten the fastening system of the diaper so that the diaper may be used as a pull-on garment when taken from the point of sale container and then later removed in the manner of a diaper.

Unfortunately, the folding registration of front and back panels required for these products is made extremely difficult due to straining of the material caused by activated elastics used to shirr the leg and waist openings. However, if the manufacturer does not activate the elastics before folding the latent elastics within the folds of the diaper, the problems of efficient heat activation of the latent elastics buried within the diaper are made difficult and are beyond the teachings of the known art. That is, if one attempts to activate latent elastic with the teachings of the known art, one will either not sufficiently activate the elastic, or will face the traditional problems of excess energy consumption, slow throughput and undesirable heating of the entire diaper.

Therefore, what is desired in the art is a method of manufacturing a folded diaper with latent elastics in the folded diaper and a way to thoroughly activate the latent elastics buried within the folded diaper quickly and economically.

SUMMARY OF THE INVENTION

In response to the difficulties and problems discussed above, a new method of manufacture for prefolded, separate diapers, and apparatus to accomplish such manufacture, have been developed.

The method comprises putting the desired latent elastic material onto the web of diaper material while the web is in the flat state, separating the individual diapers, folding each diaper in proper alignment and, in an illustrative embodiment, registering the fasteners, or front and rear panels, and fastening, or seaming, to create a waist band (collectively referred to as "fastening" hereinafter for ease of usage), and subjecting the folded, and preferably fastened, diaper to highly focused high power microwave energy, (hereinafter referred to as "microwaving" the folded diaper) to activate the latent elastic.

BRIEF DESCRIPTION OF THE DRAWINGS

FIG. 4 illustrates a mechanism for accomplishing the folding of the diaper.

FIG. 5 illustrates a resonant cavity microwave for accepting the folded diaper and activating the latent elastic therein.

DETAILED DESCRIPTION OF THE PRESENTLY PREFERRED EMBODIMENTS

Figure 1:
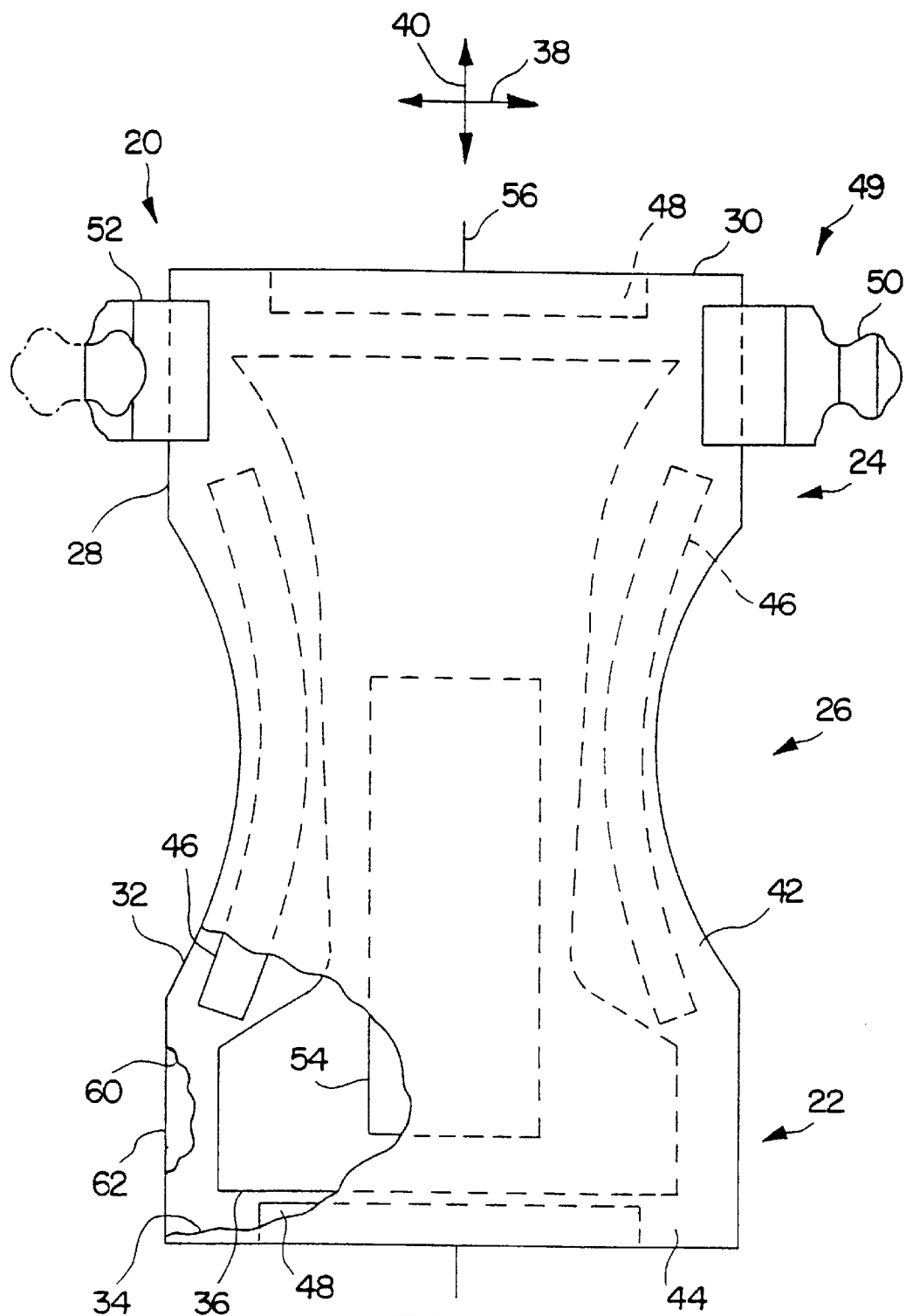
FIG. 1 shows a laid open diaper with the various parts thereof.

With reference to FIG. 1, an absorbent garment, such as the disposable diaper 20, generally defines a front waist section 22, a rear waist section 24, an intermediate, or crotch, section 26 which interconnects the front and rear waist sections, a pair of laterally opposed side edges 28, and a pair of longitudinally opposed end edges 30. The front and rear waist sections include the general portions of the article which are constructed to extend substantially over the wearers s front and rear abdominal regions, respectively, during use. The intermediate section 26 of the diaper includes the general portion of the article which is constructed to extend through the wearer's crotch region between the legs. The opposed side edges 28 define leg openings for the fastened diaper and generally are curvilinear or contoured to closely fit the legs of the wearer. The opposed end edges 30 define a waist opening for the fastened diaper and typically are straight but may also be curvilinear.

FIG. 1 is a representative plan view of the diaper 20 of the present invention in a flat, uncontracted state. Portions of the structure are partially cut away to more clearly show the interior construction of the diaper 20, and the surface of the diaper which contacts the wearer is facing the viewer. The diaper 20 includes a substantially liquid impermeable, vapor permeable, composite backsheet 32, a porous, liquid permeable topsheet 34 positioned in facing relation with the backsheet 32, and an absorbent body 36, such as an absorbent pad, which is located between the backsheet and the topsheet. The diaper 20 has a lateral direction 38 and a longitudinal direction 40. Marginal portions of the diaper 20, such as marginal sections of the backsheet 32, may extend past the terminal edges of the absorbent body 36. In the illustrated embodiment, for example, the backsheet 32 extends outwardly beyond the terminal marginal edges of the absorbent body 36 to form side margins 42 and end margins 44 of the diaper 20. The topsheet 34 is generally coextensive with the backsheet 32 but may cover an area which is larger or smaller than the area of the backsheet 32, as desired.

To provide improved fit and to help reduce leakage of body exudates from the diaper 20, the side margins 42 and end margins 44 of the diaper are elasticized with suitable leg elastic members 46 and waist elastic members 48. For example, the leg elastic members 46 may include single or multiple strands of elastic or elastomeric composites which are constructed to gather, or shirr, the side margins 42 of the diaper 20 and provide elasticized leg bands around the legs of the wearer to reduce leakage and provide improved comfort and appearance. Similarly, the waist elastic members 48 can be employed to elasticize the end margins 44 of the diaper 20 to provide elasticized waistbands.

The diaper 20, as representatively illustrated in FIG. 1, may further include a fastening system 49 illustrated by a pair of fasteners 50 which are employed to secure the diaper 20 about the waist of a wearer. Suitable fasteners 50 may include hook-and-loop type fasteners, adhesive tape fasteners, buttons, pins, snaps, mushroom-and-loop fasteners, and the like. A cooperating side panel member 52 can be associated with each fastener and may be constructed to be nonelasticized, or to be elastically stretchable at least along the lateral direction 38 of the diaper 20. In the case of training pants, additional web material may be added to the fastening system 49 and arranged under the fasteners 50 to be lightly bonded to the front waist section 22 to provide a more pant-like feel and yet be easily broken away to permit removal like a diaper.

The various components of the diaper 20 are assembled together employing various types of suitable attachment means, such as adhesive, sonic bonds, thermal bonds or combinations thereof. The diaper of FIG. 1 will be recognized by the ordinarily skilled artisan as likely to be made with its longitudinal direction in the machine direction, or direction of travel of the web. The present invention may be applied to any folded diaper, whether made with its longitudinal direction in the machine direction (FIG. 1), or in the cross machine direction as illustrated below (FIG. 4).

Figure 2:
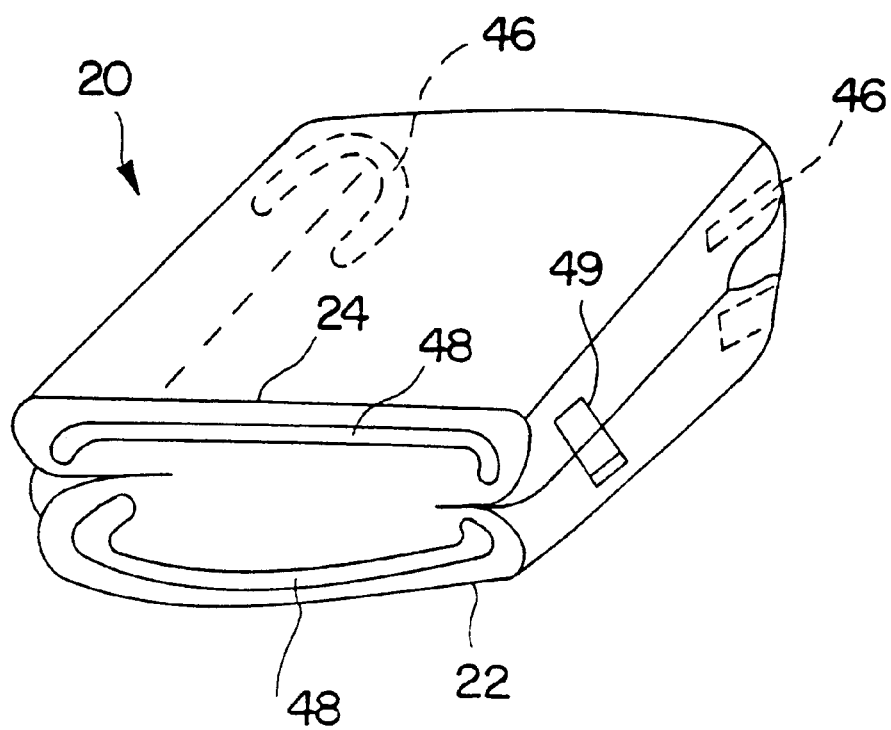
FIG. 2 is a schematic perspective view of a folded diaper.
Figure 3:
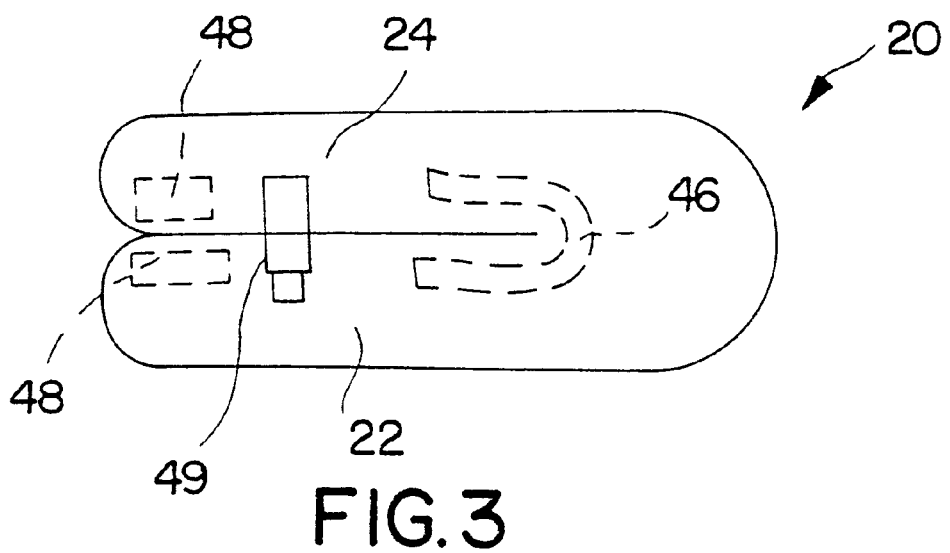
FIG. 3 is a schematic side view of a folded diaper.

Referencing FIG. 2 and FIG. 3, the diaper 20 is in a folded and pre-fastened state whereby the cooperating fastening system 49 of the front and rear waist sections 22, 24 respectively have been fastened together to form a garment which may be pulled on when taken from its point of sale container. The diaper 20 may have refastenable fastening means or seamed side panels which have been registered by folding the laid open diaper of FIG. 1 about its midline perpendicular to the longitudinal axis and bringing the respective front and back sections to mating registration and fastening them. As discussed above, this registration is only easily accomplished when the elastics are latent, i.e. unactivated and not straining the diaper.

What will be most conspicuously noticed is that the latent elastic portions 46, 48 are no longer on the surface of the diaper 20, but instead are buried within the folds thereof, requiring any activation heat for the latent elastics to penetrate the bulk of the diaper.

FIG. 4 shows an apparatus which may be used for carrying out the folding and registration of the diaper as shown in FIGS. 2 and 3. Referencing FIG. 4, a web 70 of precursor diapers is shown traveling in the machine, or X-axis direction with latent waist elastics 48 and leg elastics 46 in place indicating the long axis of the diapers is in the cross direction or Y-axis. A first rolling die cutter 72 cuts leg holes 74 in the central portion of the web. The web 70 is then transferred to a vacuum conveyor 76 to maintain the web in a tensioned state, keeping the precursor diapers flat. The web 70 is then sectioned by a second rolling die cutter 78 into individual diapers (not shown for clarity of illustration). While shown as die cutters, the leg cutting and diaper separating means are not intended to be limited to one type of cutting means. Also, e.g. the second die cutter 78 may be constructed and arranged to perform a perforation cut rather than a through cut leaving the diapers defined individually but needing to be separated by tensioning forces on the rotary wheel 80.

The individual diapers (or perforated web) are fed through a counter roller 82 and picked up by a horizontal-to-vertical twisted belt 84 running on either side of an inclined folding projection 86 leading to the rotary wheel 80. The counter roller 82 or other suitable means may be used to apply a microwave sensitive solution such as set forth in U.S. Pat. No. 5,916,203 as indicated by feedline 108 connected to reservoir 110. The diaper is folded in an inverted "V", shape with its crotch area up and with waist band areas down by the time the diaper reaches the rotary wheel 80 to be accepted by open, inverted "V" shaped protrusions 88 on the wheel. An inverted "V" 90 in the drawing indicates the diaper orientation on the inclined folding projection 86.

The diaper may be held in place on the protrusions 88 by vacuum or other suitable means. While the rotary wheel 80 is turning with the diaper 20, the fasteners of the front and rear panels are aligned and closed or fastened together. Mechanical armatures such as modified versions of the apparatus set forth in U.S. Pat. No. 4,650,530 to Mahoney et al., which is incorporated herein to the extent necessary for understanding the present invention, may suitably accomplish the folding and may be assisted by controlled vacuum slots or the like within the protrusions 88. The prefastened diaper presents its leg holes to a pair of orbital pickers, collectively 96, which engage the leg holes and remove the fastened diaper from rotary wheel 80 and place it in a vertical-to-horizontal twisted removal belt 98 which carries the diaper to an elastic activation apparatus 100 (FIG. 5) according to the present invention. It will be appreciated that where the fastening system 50 of diaper 20 extends undesirably beyond the basic rectangular shape of the folded diaper when fastened, the extended portions of the prefastened fastening system may also be tucked into the body of the diaper at the exit of the removal belt 98 according to known apparatus to present a clean rectangular form to the elastic activation apparatus 100.

Referencing FIG. 5 the activation apparatus 100 consists of a diaper conveyor assembly 102 for carrying the folded diaper 104 through a resonant cavity microwave heating chamber 106 at about 366 m/min. or 1200 ft/min., or other commercially viable selected speed. Taking an average sized diaper through a six inch focused power spot of the resonant cavity 106 results in exposing the diaper 104 to microwave energy for about 0.025 seconds. In order to activate the latent elastics it is recommended that power be at least in the range of above 1 KW to about 30 KW. Per above, in one method of activating the latent elastics, the latent elastic areas are treated with a microwave sensitive solution of water, polyethylene glycol, and sorbitol; but are otherwise desirably kept at a low moisture content so as to not heat the whole diaper and rob available energy from the heating of the latent elastics.

Words of degree, such as "about", "substantially", and the like are used herein in the sense of "perfectly, or nearly perfectly, when given the manufacturing and material tolerances inherent in the stated circumstances" and are used to prevent the unscrupulous infringer from unfairly taking advantage of the invention disclosure where exact or absolute figures are stated as an aid to understanding the invention.

While in the foregoing specification this invention has been described in relation to certain preferred embodiments thereof, and many details have been set forth for purpose of illustration, it will be apparent to those skilled in the art that the invention is susceptible to additional embodiments and that certain of the details described herein can be varied considerably without departing from the basic principles of the invention.

We claim:

1. A method for making a pre folded diaper, comprising:
   a) running a web of diaper material in a machine direction;
   b) applying latent elastic material to the web of diaper material;
   c) cutting the web in a cross machine direction to define individual diapers;
   d) folding said individual diapers to a folded position at an intermediate section of the diapers along a medial line of a longitudinal axis of the diaper; and
   e) microwaving the folded diaper to activate the latent elastic.

2. The method for making a prefolded diaper according to claim 1, further comprising: treating the diaper with a microwave sensitive material to induce heat transfer to the latent elastic.

3. The method for making a prefolded diaper according to claim 2, further comprising: microwaving the prefolded diaper in a single microwave resonant chamber.

4. The method for making a prefolded diaper according to claim 3, further comprising: microwaving the prefolded diaper in an single microwave resonant chamber which has a focused power spot about 6 inches long.

5. The method for making a prefolded diaper according to claim 3, further comprising: microwaving the prefolded diaper in an single microwave resonant chamber at a transit speed of greater than 300 meters/minute.

6. The method for making a prefolded diaper according to claim 5, further comprising: microwaving the prefolded diaper in an single microwave resonant chamber at a transit speed of about 366 meters/minute.

7. The method for making a prefolded diaper according to claim 3, further comprising: microwaving the prefolded diaper in an single microwave resonant chamber at an energy of greater than 500 watts.

8. The method for making a prefolded diaper according to claim 7, further comprising: microwaving the prefolded diaper in an single microwave resonant chamber at an energy in the range of greater than 1 kilowatt to about 30 kilowatts.

9. The method for making a prefolded diaper according to claim 1, further comprising: microwaving the prefolded diaper for less than about 0.08 seconds.

10. The method for making a prefoided diaper according to claim 9, further comprising: microwaving the prefolded diaper for about 0.025 seconds.

11. The method for making a prefolded diaper according to claim 1, further comprising: microwaving the prefolded diaper in a single microwave resonant chamber.

12. The method for making a prefolded diaper according to claim 11, further comprising: microwaving the prefolded diaper in an single microwave resonant chamber with a focused power spot of about 6 inches long.

13. The method for making a prefolded diaper according to claim 11, further comprising: microwaving the prefolded diaper in an single microwave resonant chamber at an energy of greater than 500 watts.

14. The method for making a prefolded diaper according to claim 13, further comprising: microwaving the prefolded diaper in an single microwave focus chamber at an energy in the range of greater than 1 kilowatt to about 30 kilowatts.

15. The method for making a prefolded diaper according to claim 11, further comprising: microwaving the prefolded diaper in an single microwave resonant chamber at a transit speed of greater than 300 meters/minute.

16. The method for making a prefolded diaper according to claim 15, further comprising: microwaving the prefolded diaper in an single microwave resonant chamber at a transit speed of about 366 meters/minute.

17. The method for making a prefolded diaper according to claim 2, further comprising: microwaving the prefolded diaper for less than about 0.08 seconds.

18. The method for making a prefolded diaper according to claim 17, further comprising: microwaving the prefolded diaper for about 0.025 seconds.

19. A method for making a prefolded diaper, comprising:
   a) running a web of diaper material in a machine direction;
   b) applying latent elastic material to the web of diaper material;
   c) cutting the web in a cross machine direction to define individual diapers;
   d) folding said individual diapers to a folded position at an intermediate section of the diapers along a medial line of a longitudinal axis of the diaper;
   e) folding side margins of the front and rear waist sections of each lateral side of the folded diaper together and fastening the front and rear waist sections together thereby creating a prefastened diaper; and
   f) microwaving the prefastened diaper to activate the latent elastic.

20. The method according to claim 19 wherein the fastening step includes seaming the front and rear waist sections together.

21. The method according to claim 19 wherein the fastening step includes fastening the front and rear waist sections together with a refastenable fastening system.

22. The method according to claim 19 further including microwaving the folded diaper in a single microwave focus chamber for less than about 0.08 seconds at a transit speed of greater than 300 meters/minute at an energy of greater than 500 watts.

23. A method for making a prefolded diaper, comprising:
   a) running a web of diaper material in a machine direction;
   b) applying latent elastic material to the web of diaper material;
   c) cutting the web in a cross machine direction to define individual diapers;
   d) folding said individual diapers to a folded position at an intermediate section of the diapers along a medial line of a longitudinal axis of the diaper;
   e) folding refastenable fastening means of the front and rear waist sections of each lateral side of the folded diaper together in lapping relationship and fastening the front and rear waist sections together thereby creating a prefastened diaper;
   f) treating the diaper material with a microwave sensitive material to induce heat transfer to the latent elastic; and
   g) microwaving the prefastened diaper to activate the latent elastic in a single microwave resonant chamber at a transit speed of about 366 meters/minute at an energy in the range of greater than 1 kilowatt to about 30 kilowatts.

* * * * *